US010045829B1

(12) United States Patent
Norman et al.

(10) Patent No.: US 10,045,829 B1
(45) Date of Patent: Aug. 14, 2018

(54) OBSTETRIC HEMORRHAGE CART

(71) Applicant: Neonatal Product Group, Inc., Stillwell, KS (US)

(72) Inventors: Scott Norman, Stillwell, KS (US); Mark Petheram, Olathe, KS (US); Heather Fibuch-Townsend, Leawood, KS (US); Anthony Hash, Olathe, KS (US)

(73) Assignee: Neonatal Products Group, Inc., Stillwell, KS (US)

( * ) Notice: Subject to any disclaimer, the term of this patent is extended or adjusted under 35 U.S.C. 154(b) by 0 days.

(21) Appl. No.: 15/728,639

(22) Filed: Oct. 10, 2017

(51) Int. Cl.
*A47B 31/02* (2006.01)
*A61B 50/10* (2016.01)
*A61B 50/13* (2016.01)
*A47B 81/00* (2006.01)
*A47B 96/00* (2006.01)
*A61M 5/14* (2006.01)
(Continued)

(52) U.S. Cl.
CPC .............. *A61B 50/13* (2016.02); *A47B 31/00* (2013.01); *A47B 31/02* (2013.01); *A47B 81/00* (2013.01); *A47B 96/00* (2013.01); *A61B 90/35* (2016.02); *A61G 12/001* (2013.01); *A61G 15/14* (2013.01); *A61M 5/1417* (2013.01); *G01G 17/04* (2013.01); *G01G 21/28* (2013.01); *A47B 2031/003* (2013.01); *A47B 2031/006* (2013.01); *A47B 2200/0091* (2013.01); *A47B 2220/0077* (2013.01); *A61B 2050/0014* (2016.02); *A61G 2200/12* (2013.01); *A61G 2203/20* (2013.01); *A61G 2210/00* (2013.01); *A61M 2205/505* (2013.01)

(58) Field of Classification Search
CPC ......... A47B 31/00; A47B 31/02; A47B 81/00; A47B 96/00; A47B 2031/003; A47B 2031/006; A47B 2200/0077; A47B 2200/0091; A61B 50/10; A61B 50/13; A61B 90/35; A61G 12/001; A61G 15/14; A61M 5/1417; G01G 17/04; G01G 21/28
USPC ............ 312/209, 249.1, 249.8, 249.11, 280; 62/440, 457.1, 457.9; 280/47.34, 47.35; 177/144
See application file for complete search history.

(56) References Cited

U.S. PATENT DOCUMENTS 3,715,148 A * 2/1973 Beals ..................... A47B 31/00
312/209
3,893,740 A * 7/1975 England ................ E05B 65/467
312/216

(Continued)

*Primary Examiner* — James O Hansen
(74) *Attorney, Agent, or Firm* — Hovey Williams LLP

(57) ABSTRACT

A obstetric hemorrhage cart having a chassis riding on wheels, drawers supported by the chassis, a cooling apparatus such as a refrigerator in the chassis, a locking bar pivotally attached to the chassis, a scale drawer, a scale mounted in the scale drawer, and a positionable task light attached to the chassis. Each of the drawers may include a drawer lock shiftable between a locked position and an unlocked position. The locking bar may be lockable in a blocking orientation and shiftable to a non-blocking orientation when unlocked, thus serving as a secondary safety lock preventing the drawers and a cooling apparatus door from inadvertently opening during travel. The scale may have a weight surface and a scale display, and the scale drawer may have a window for viewing the scale display from a front of the chassis when the scale drawer is open.

20 Claims, 10 Drawing Sheets

(51) Int. Cl.
*A61B 90/35* (2016.01)
*G01G 17/04* (2006.01)
*G01G 21/28* (2006.01)
*A61G 12/00* (2006.01)
*A61G 15/14* (2006.01)
*A47B 31/00* (2006.01)
*A61B 50/00* (2016.01)

(56) References Cited

U.S. PATENT DOCUMENTS

| | | | | |
|---|---|---|---|---|
| 4,114,965 A * | 9/1978 | Oye | A47B 31/00 312/209 |
| 5,314,244 A * | 5/1994 | Swets | E05B 65/467 211/181.1 |
| 5,518,310 A * | 5/1996 | Ellman | A61G 12/001 312/209 |
| 6,371,584 B1 * | 4/2002 | Alreck | A47B 67/04 177/144 |
| 6,802,578 B1 * | 10/2004 | Lang | A47B 46/00 177/144 |
| 8,075,071 B1 * | 12/2011 | Whittall | A47B 23/043 312/209 |
| 2002/0070847 A1 * | 6/2002 | Hamilton | A61G 12/001 340/309.16 |
| 2006/0022560 A1 * | 2/2006 | Ashby | E05B 65/467 312/216 |
| 2006/0284526 A1 * | 12/2006 | Pathmanathan | A47B 46/00 312/228.1 |
| 2007/0228680 A1 * | 10/2007 | Reppert | A47B 21/00 280/47.35 |
| 2008/0036343 A1 * | 2/2008 | Wang | A47B 67/04 312/283 |
| 2010/0026151 A1 * | 2/2010 | Melkumyan | B25H 1/02 312/249.11 |
| 2010/0145160 A1 * | 6/2010 | Cinqualbre | A61L 2/0088 600/300 |
| 2013/0277930 A1 * | 10/2013 | Ergun | G06F 1/1607 280/47.35 |
| 2014/0353998 A1 * | 12/2014 | White | B60P 3/0257 296/22 |
| 2016/0095779 A1 * | 4/2016 | Canady | B62B 3/104 280/79.2 |

\* cited by examiner

OBSTETRIC HEMORRHAGE CART

BACKGROUND

Obstetric hemorrhaging is a leading cause of preventable maternal morbidity and mortality. Medical professionals often lack the required tools or accurate and consistent standards for estimating and tracking a patient's blood loss. If blood loss is underestimated or not recognized soon enough, there may be critical delays in necessary treatment. Additionally, time spent retrieving supplies, ultrasound equipment, or even transporting a patient to an operating room can result in preventable deaths.

One way to save valuable time is through the use of mobile carts in birthing rooms for transporting and making readily available various medical supplies including blood, pharmaceuticals, and breast milk. However, existing carts are often generically designed for a wide-range of hospital needs and do not fully address the unique challenges of efficiently and accurately diagnosing and treating obstetric hemorrhaging.

Accordingly, there is a need for an improved cart that meets the specific needs of medical professionals in obstetric hemorrhage situations.

SUMMARY

The present invention solves the above-described problems and provides a distinct advance in the art by providing a mobile cart specifically designed for post-partum hemorrhaging scenarios. More particularly, the present invention provides an obstetric hemorrhage cart for diagnosis, tracking, and/or treatment during obstetric hemorrhaging that enables the storage and transportation of medical supplies in a highly-organized and secure manner.

An obstetric hemorrhage cart constructed according to one embodiment of the present invention broadly includes a chassis, a plurality of wheels, a plurality of supply drawers, a cooling apparatus, a locking bar, a task light, a power supply, a scale drawer, and a scale mounted in the scale drawer. Specifically, the chassis may have a base, a top surface opposing the base and composed of an antimicrobial material, two opposing side walls, a front wall, and a back wall, with the plurality of wheels attached to the chassis at the base. Furthermore, a handle may be attached to the chassis for pushing or pulling the cart to travel on its wheels. The side walls may include a plurality of drawer mounts mechanically attached thereto. These drawer mounts may be reconfigurable along a height of the side walls. The supply drawers may each slidably attach to one or two of the drawer mounts, and the supply drawers may each include a drawer lock shiftable between a locked position preventing opening thereof and an unlocked position allowing opening thereof.

The cooling apparatus may include a storage compartment with a cooling apparatus door shiftable between an open position and a closed position. The cooling apparatus may also include a cooling apparatus door lock shiftable between a locked position preventing the cooling apparatus door from opening and an unlocked position allowing the cooling apparatus door to open. The cooling apparatus may also include refrigerating components that cool a temperature of the storage compartment to a predetermined temperature. The locking bar may be pivotally attached to the chassis and shiftable between a blocking orientation simultaneously preventing opening of the supply drawers and the cooling apparatus door and a non-blocking orientation allowing the supply drawers and the cooling apparatus door to open. The locking bar may also be selectively lockable in the blocking orientation.

The scale drawer may be slidable into the chassis at one of the side walls of the chassis in a closed position and slidable out of that one of the side walls in an open position. The scale may include a weighing surface and a scale display. T scale may be fixed within the scale drawer, and the scale drawer may further include a transparent sidewall or window through which the scale display is viewable by a person facing the front of the chassis when the scale drawer is in the open position. The weighing surface of the scale may also include or be attachable to an open-topped enclosure for receiving materials to be weighed by the scale. Furthermore, a disposable hazardous waste bag may be attached to the open-topped enclosure and sized and configured to substantially surround a majority of the scale drawer when the scale drawer is open and the open-topped enclosure is mounted to the scale.

The task light may be attached to the chassis and have a jointed, adjustable light stand connected to one or more light bulbs. The portable power supply may be a rechargeable uninterruptible power supply (UPS) mounted within the chassis and behind the supply drawers and may be electrically coupled to the cooling apparatus, the scale, and/or the task light. Furthermore, a power strip of outlets may be mounted to the back wall of the chassis and electrically coupled with the portable power supply, thus allowing other electronic devices and accessories to be plugged into and powered by the power source of the cart. Some embodiments of the cart may further include an IV pole fixed to the chassis and having a height adjustment mechanism and an electronic display physically coupled to the IV pole or the chassis. The electronic display may be electrically coupled to the portable power supply and may communicably couple with a portable ultrasound machine.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the present invention will be apparent from the following detailed description of the embodiments and the accompanying drawing figures.

BRIEF DESCRIPTION OF THE DRAWING FIGURES

Embodiments of the present invention are described in detail below with reference to the attached drawing figures, wherein.

Figure 1:
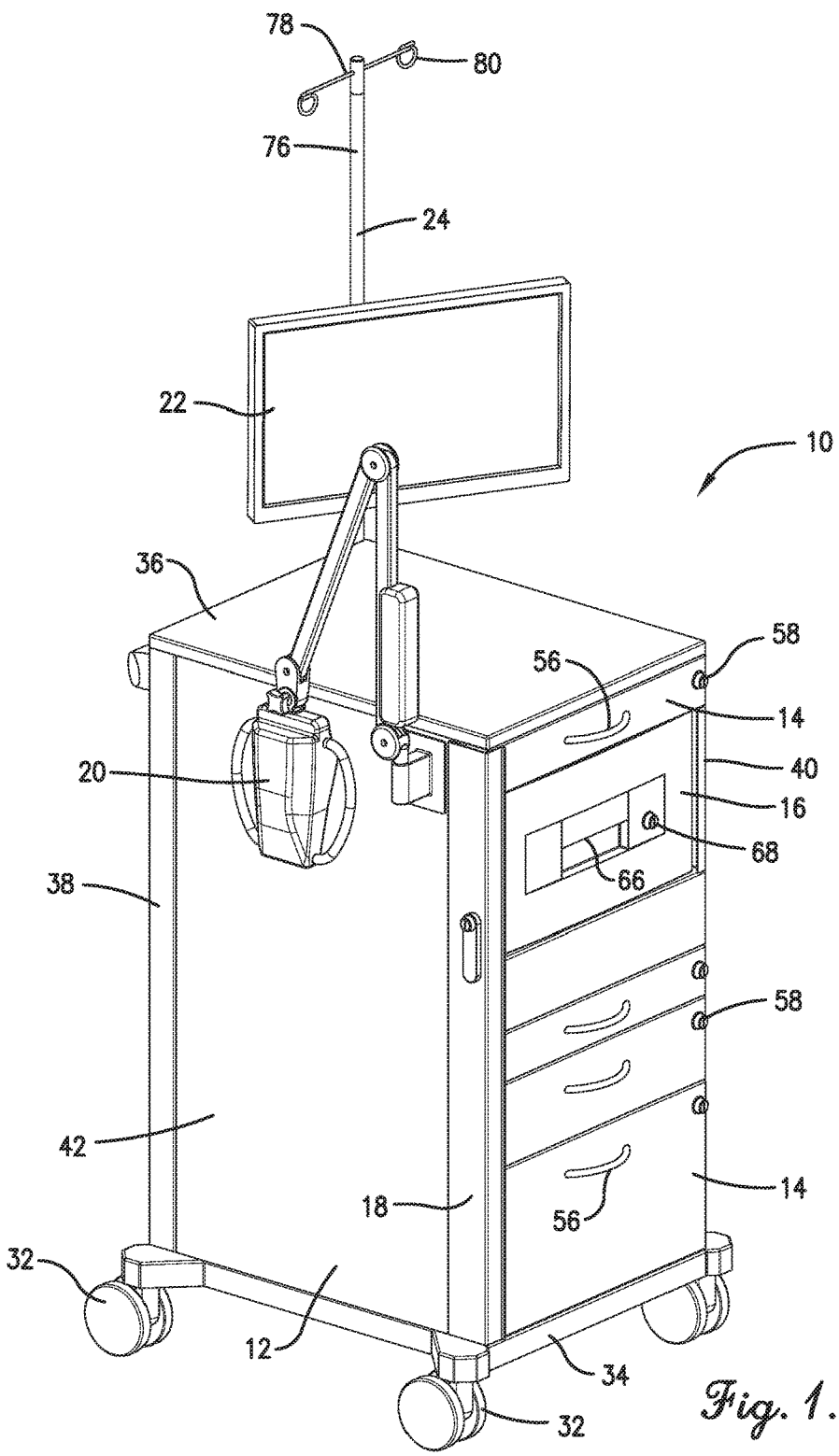
FIG. 1 is a perspective view of an obstetric hemorrhage cart constructed in accordance with an embodiment of the present invention.
Figure 2:
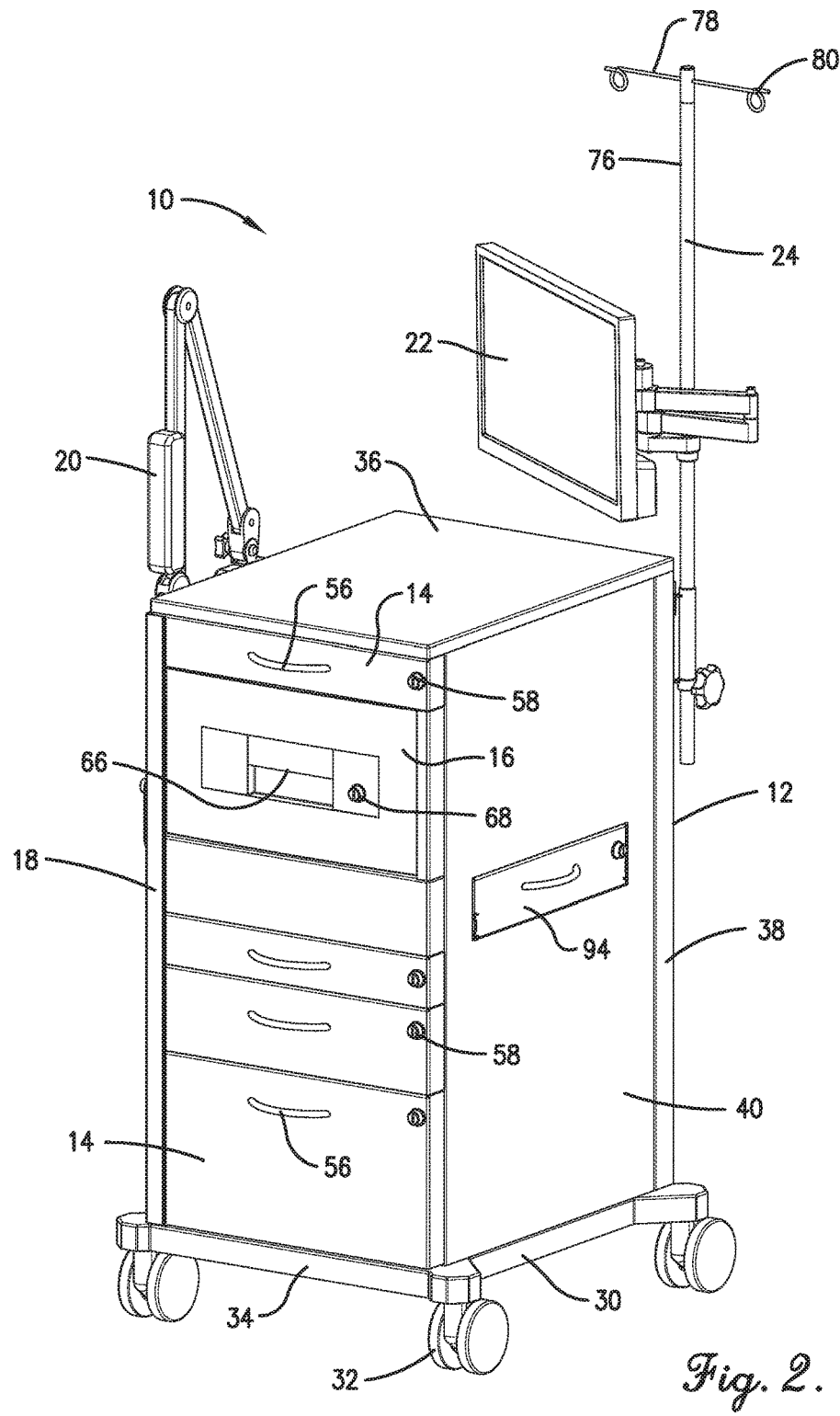
FIG. 2 is a front-side perspective view of the cart of FIG. 1.

The drawing figures do not limit the present invention to the specific embodiments disclosed and described herein. The drawings are not necessarily to scale, emphasis instead being placed upon clearly illustrating the principles of the invention.

DETAILED DESCRIPTION OF THE EMBODIMENTS

The following detailed description of the invention references the accompanying drawings that illustrate specific embodiments in which the invention can be practiced. The embodiments are intended to describe aspects of the invention in sufficient detail to enable those skilled in the art to practice the invention. Other embodiments can be utilized and changes can be made without departing from the scope of the present invention. The following detailed description is, therefore, not to be taken in a limiting sense. The scope of the present invention is defined only by the appended claims, along with the full scope of equivalents to which such claims are entitled.

In this description, references to "one embodiment", "an embodiment", or "embodiments" mean that the feature or features being referred to are included in at least one embodiment of the technology. Separate references to "one embodiment", "an embodiment", or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the present technology can include a variety of combinations and/or integrations of the embodiments described herein.

Turning now to the drawing figures, and particularly FIGS. 1-6, an obstetric hemorrhage cart 10 constructed in accordance with a preferred embodiment of the invention is illustrated. The cart 10 broadly includes a chassis 12, a plurality of supply drawers 14, a cooling apparatus 16, a locking bar 18, a positionable task light 20, a display 22, an IV pole 24, a power source 26, and/or a scale 28. The location and combination of these components on a single portable cart 10 as described herein may advantageously reduce critical response time in obstetric bleeding situations by up to several minutes.

Figure 7:
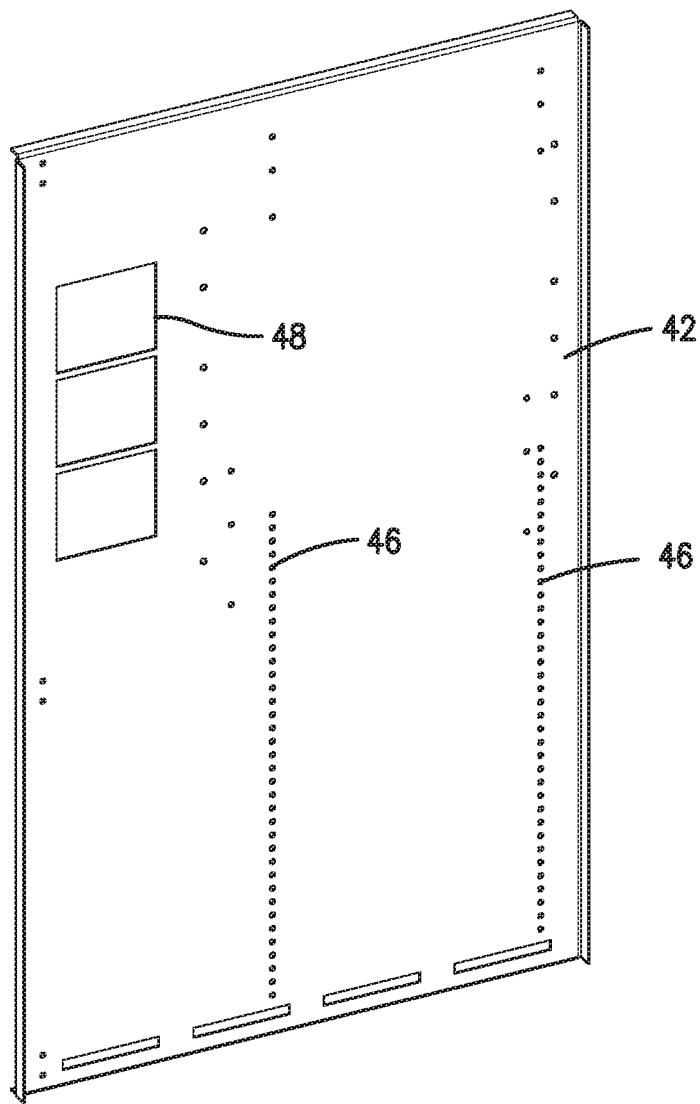
FIG. 7 is a side perspective view of a side wall of the cart of FIG. 1, illustrating mounting holes and ventilation holes formed therethrough.

The chassis 12 may include a frame 30 and a plurality of wheels 32 on which the frame 30 may travel. The frame 30 may be configured for attaching various components of the cart 10. For example, the frame 30 may include a base 34, a top surface 36 opposite the base 34, a back wall 38, an opposing front wall 40, and two opposing side walls 42,44, all of which join to enclose a space within the chassis 12. In some embodiments of the invention, as illustrated in FIG. 7, the side walls 42,44 may include a plurality of mounting holes 46 and ventilation holes 48, allowing reconfigurability or customization of the supply drawers 14, using any quantity and size of supply drawers 14. The plurality of ventilation holes 48 can likewise allow the cooling apparatus 16 to be repositioned along a height of the chassis 12, while still providing an opening through which hot air from the cooling apparatus 16 may be expelled. In some embodiments of the invention, at least one of the side walls 42,44 may include an outer panel and an inner panel spaced apart from each other, with the inner panel including the ventilation holes such that heat expelled from the cooling apparatus 16 through the ventilation holes is forced between the inner and outer panels and exits into the space within the chassis 12 through one of the other holes along the inner panel, above or below the cooling apparatus 16.

Figure 3:
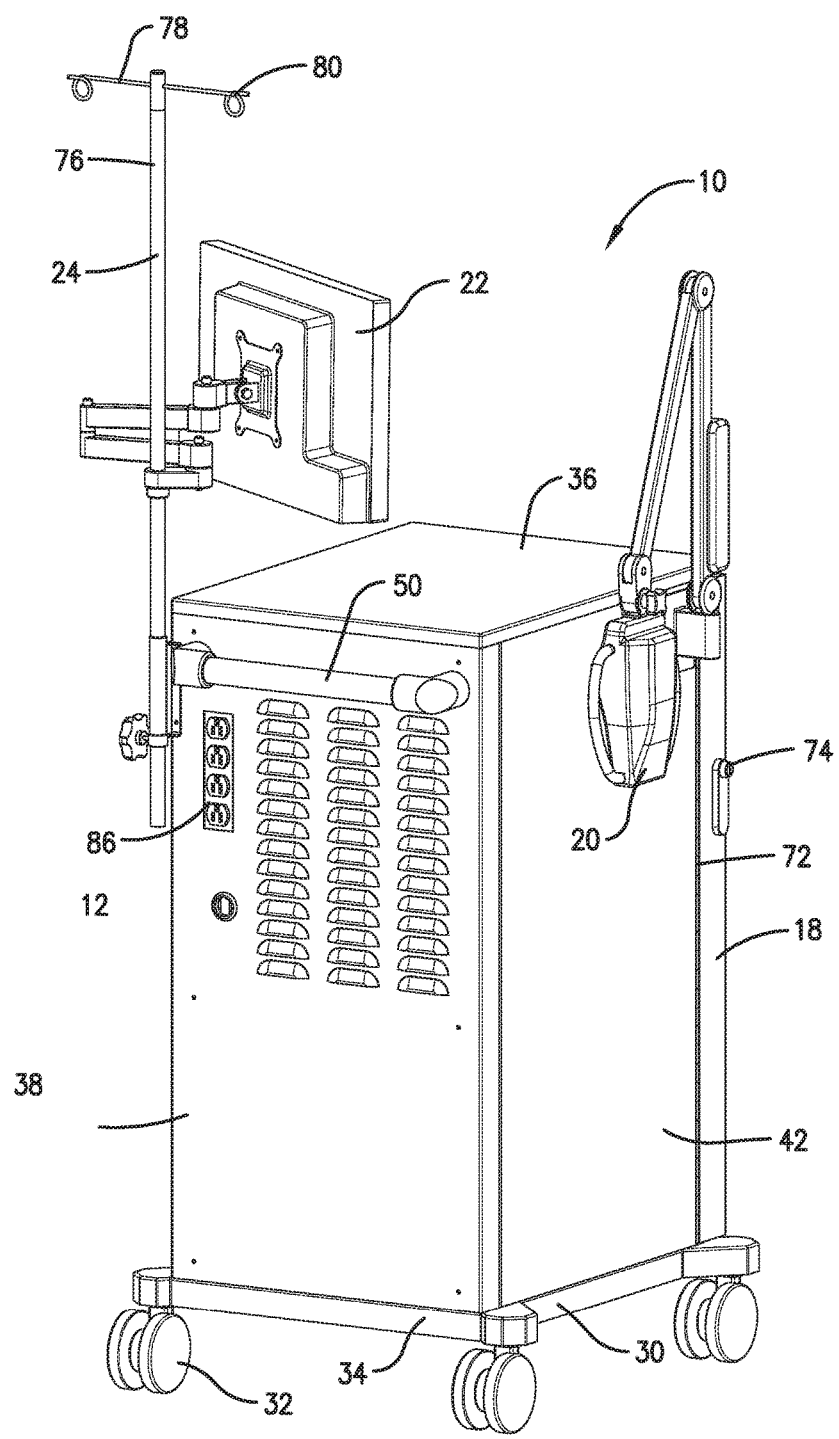
FIG. 3 is a back perspective view of the cart of FIG. 1.

The front wall 40 and at least one of the side walls 42,44 may have one or more openings formed therein, allowing the supply drawers 14 to slide into and out of the chassis 12, as well as providing access to the cooling apparatus 16. The plurality of wheels 32 may include four wheels and may be attached to the base. However, the chassis 12 may include any quantity of wheels without departing from the scope of the invention. In some embodiments of the invention, as illustrated in FIG. 3, the chassis 12 may also include a handle 50 attached to one of the side walls, the front wall, and/or the back wall.

Figure 8:
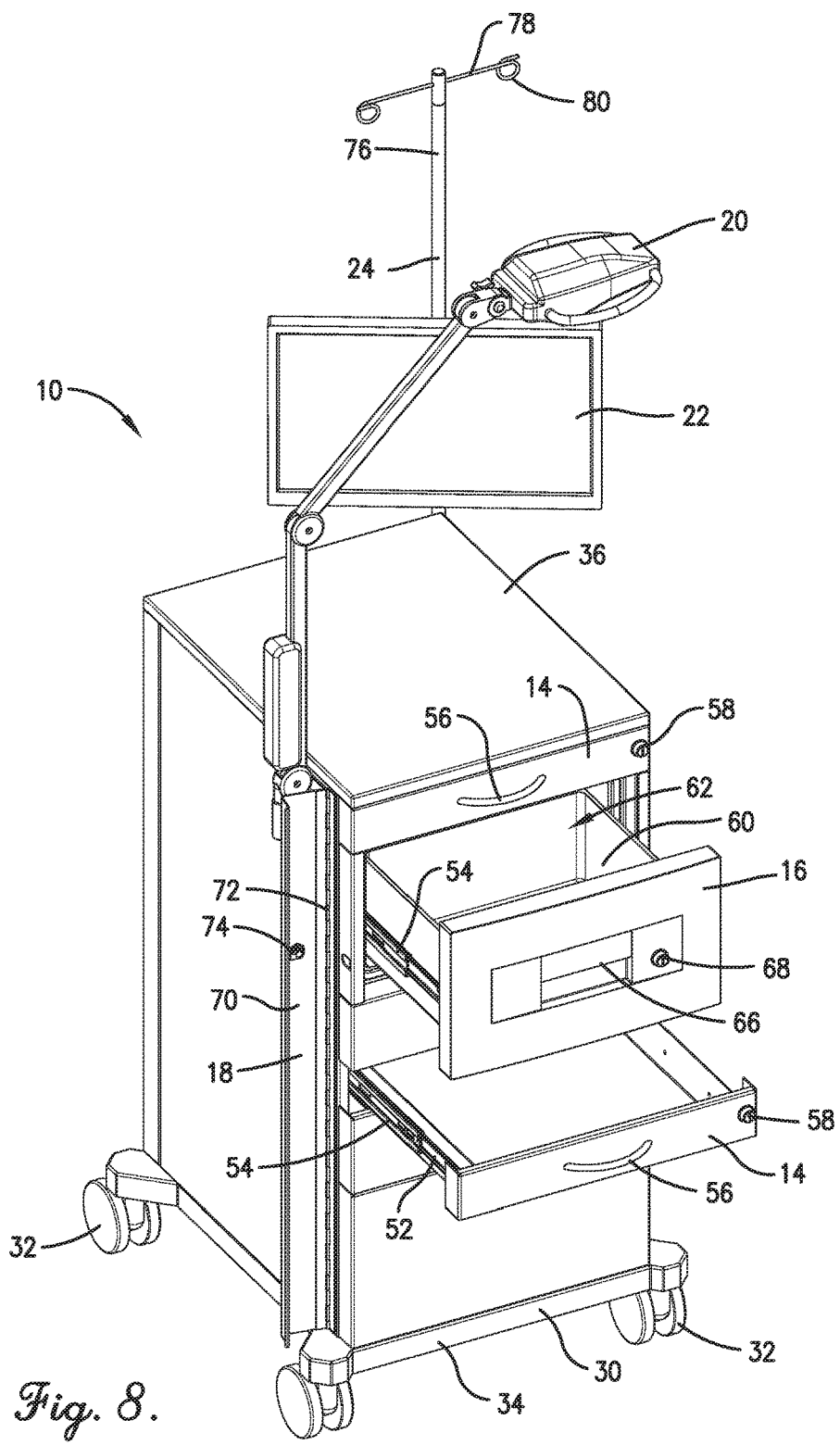
FIG. 8 is a front-top perspective view of the cart of FIG. 1 with open drawers and a locking bar pivoted to a disengaged position.
Figure 9:
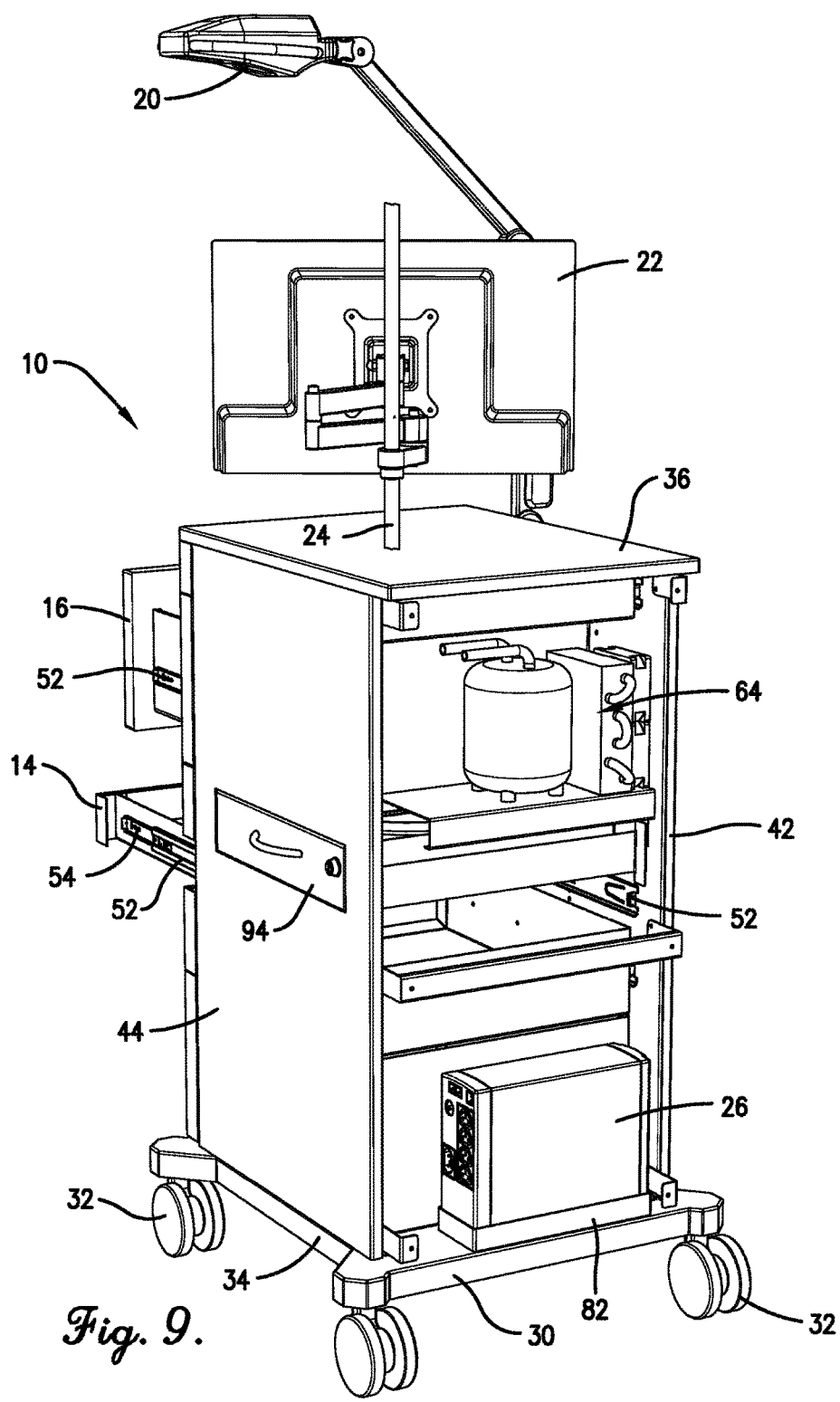
FIG. 9 is a back perspective view of the cart of FIG. 1 with a back wall removed to illustrate components housed therein.

As illustrated in FIGS. 8-9, the chassis 12 may further comprise drawer mounts 52 installed within the frame 30, such as along interior surfaces of the front, back, or side walls 38,40,42,44 and/or along the base 34 or top surface 36 of the frame 26. Specifically, the drawer mounts 52 may be installed in any combination along a height of the chassis 12. The drawer mounts 52 may have a uniform height between each pair of drawer mounts 52, or the drawer mounts 52 may have different heights between each pair of drawer mounts 52. The drawer mounts 52 may include rails, ledges, or other protrusions or depressions sized, shaped, and oriented for supporting the supply drawers 14 and/or allowing the drawers to slide into and out of the chassis 12. For example, the drawer mounts 42 may include rails that are screwed into or otherwise anchored to the holes 46 formed into the side walls 42,44 of the chassis 12, as described above. By screwing the drawer mounts 44 into a different set of the side wall holes 46, the supply drawers 14 of the cart 10 may be reconfigured or exchanged for different sizes of drawers.

One or more surfaces of the chassis 12, such as the top surface 36 or the handle 50, may be constructed of an antimicrobial material and/or completely or partially coated with an antimicrobial material. The antimicrobial material may be any material that inhibits the growth of pathogenic microorganisms such as bacteria, fungi, yeast, and algae. The material may be a metal such as copper, silver, gold, etc., or an alloy such as brass, bronze, cupronickel, copper-nickel-zinc or others. Additionally or alternatively, the material may be polymers, polymeric biocides, organosilanes, or the like. In some embodiments of the invention, an underside of the top surface 36 of the chassis 12 may have a notch formed or molded therein, into which a locking mechanism may extend for locking a top-most one of the supply drawers 14 or the cooling apparatus 16.

The plurality of supply drawers 14 are provided as supply storage compartments for the various medical supplies, such as medications, intravenous fluids, blood for transfusions, a portable ultrasound machine, and the scale. The supply drawers 14 may each include a front wall, a back wall, opposing side walls, and a bottom wall forming a container with an open top through which supplies may be accessed. The supply drawers 14 may each also include a handle 56 attached to or integrally formed with the front wall thereof. Furthermore, the supply drawers 14 may each include drawer slides 54. The drawer slides 54 may be attached to exterior surfaces of the side walls of the supply drawers 14 and may be configured to slidably engage the drawer mounts 52 installed in the chassis 12. Specifically, the drawer slides 54 may include wheels, rails, protrusions, indentions, or other elements configured for slidably engaging with the drawer mounts. When one of the supply drawers 14 is slid into an open orientation, a user may access supplies therein through the open top thereof. Likewise, when one of the supply drawers 14 is slide into a closed orientation, a user is prevented from accessing supplies therein through the top thereof. In some embodiments of the invention, the drawer mounts 52 and drawer slides 54 may be configured to be interchangeable so that any drawer slide 54 can slidably engage any drawer mount 52, allowing for a variety of drawer sizes and configurations.

In some embodiments of the invention, one or more of the supply drawers 14 may include a lock 58. The lock 58 may be shiftable between a locked and an unlocked position. When the lock 58 is in the locked position, it prevents its supply drawer 14 from opening. When in the unlocked position, the lock 58 allows its supply drawer 14 to open. The lock 58 may be any locking mechanism, such as a lock-and-key system, a digital lock, a magnetic lock, or any drawer-locking device known in the art for preventing unauthorized access to one or more of the supply drawers 14.

The cooling apparatus 16 may be a refrigeration unit provided for storing medical items that have temperature-related sensitivities, such as containers of blood for transfusions, intravenous fluids, prescription drugs, or other medication. As illustrated in FIGS. 8-9, the cooling apparatus 16 may comprise a storage compartment 60 with an open front, a door 62 openable for accessing items in the cooling apparatus 16, and other standard refrigerating components 64 for cooling the space within the storage compartment 60. For example, the cooling apparatus 16 may include a compressor, condenser coils, evaporator coils, fans, pipes, valves, a thermostat for keeping the storage compartment within a predetermined tolerance of user-selected temperature, and the like. In some embodiments of the invention, the cooling apparatus 16 may additionally or alternatively include a freezer or any other cooling compartment known in the art for cooling supplies therein. Some components of the cooling apparatus 16 may be electrically coupled to the power source, providing electrical power for operation thereof.

The cooling apparatus door 62 may be pivotally attached to the storage compartment 60 or may include a drawer shiftable between an open and a closed position. For example, the cooling apparatus door 62 may be a drawer including a front wall with a handle 66 attached thereto or integrally formed therewith, a back wall opposite the front wall, two opposing side walls extending between the front and back walls thereof, and a bottom wall, cooperatively forming a container with an open top. The cooling apparatus door 62 may also include a lock 68 shiftable between a locked position and an unlocked position. In the locked position, the lock may prevent the cooling apparatus door 62 from opening, while in the unlocked position, the lock 54 may allow the cooling apparatus door 62 to open. The lock 68 may be any locking mechanism known in the art, such as a lock-and-key system, a digital lock, a magnetic lock, or any locking device known in the art for preventing unauthorized access to contents within the storage compartment 60 of the cooling apparatus 16.

Figure 4:
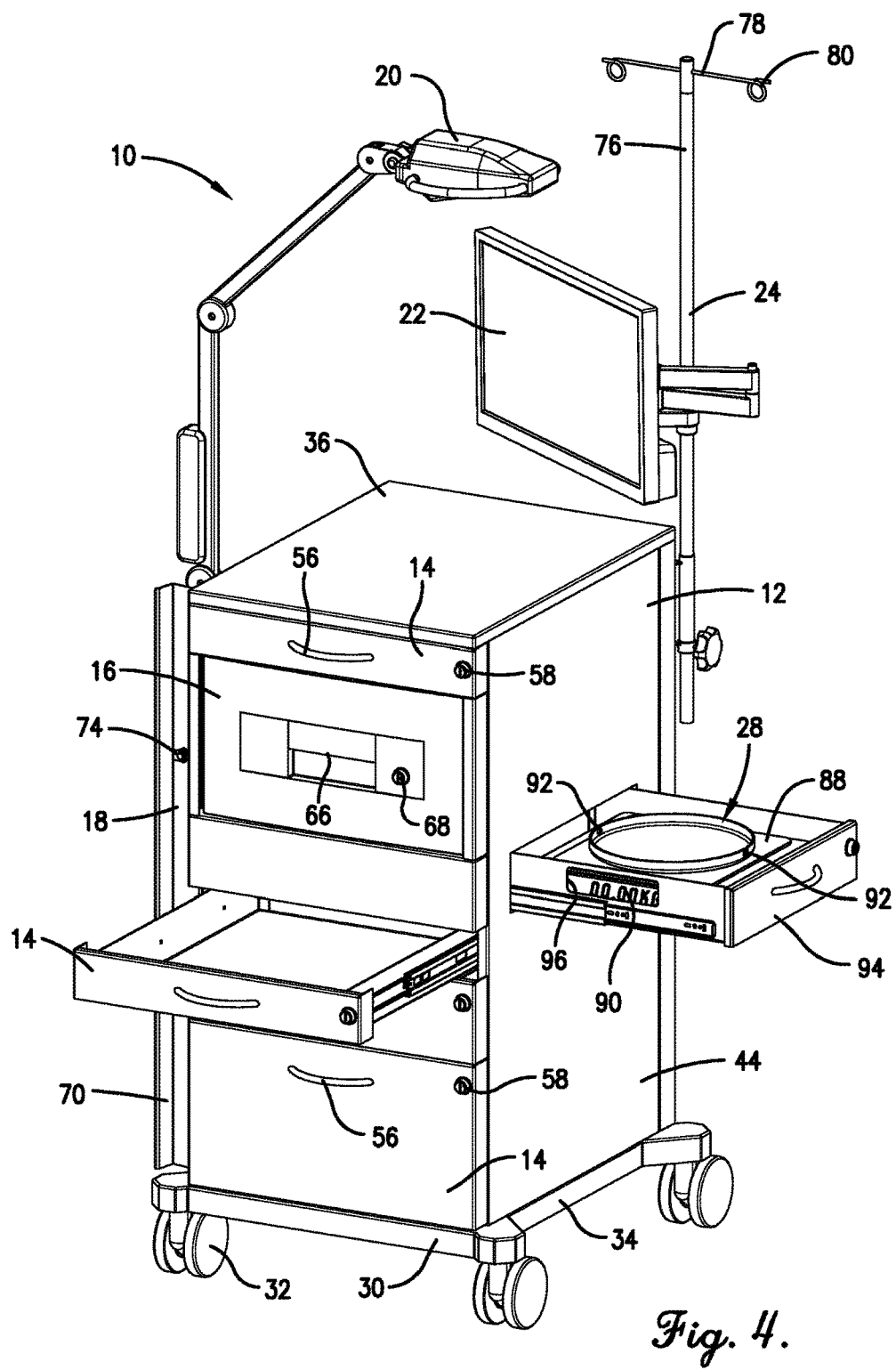
FIG. 4 is a front-side perspective view of the cart of FIG. 1 with a scale drawer in an open position.

As illustrated in FIGS. 1, 4, and 8, the locking bar 18 of the cart 10 may include a flange 70, hinges 72, and a locking mechanism 74 and may be used to. The flange 70 may be a long, flat strip of rigid material or may be a long, right-angled strip of rigid material. The flange 70 may substantially extend an entire height of the chassis 12 or otherwise span a distance of a plurality of the supply drawers 14 and/or the cooling apparatus door. In some embodiments of the invention, the flange 70 may be pivotally attached at or proximate to a corner of the chassis 12 where one of the side walls connects with the front wall. The flange 70 may be pivotally attached to the chassis 12 via the hinges 72, and may be pivotally actuatable between a blocking orientation blocking the supply drawers 14 and the cooling apparatus door 62 from opening, as illustrated in FIG. 1, and a non-blocking orientation that does not block the supply drawers 14 from opening, as illustrated in FIGS. 4 and 8. The hinges 72 may be any jointed or flexible mechanical device known in the art for allowing pivoting about a pivot point. Additionally or alternatively, in some embodiments of the invention, the locking bar 18 may be pivotally attached to a rod or rigid elongated cylinder and pivots about an axis thereof.

The locking mechanism 74 may include a lock-and-key system, a digital lock, a keypad, a magnetic lock, and/or any device known in the art for selectively preventing pivoting of the flange 70 about the hinges 72. For example, the locking mechanism 74 may be any keypad known in the art, such as a digital keypad, a set of combination disks, or the like. The locking mechanism 74 may be actuatable between an engaged position and a disengaged position using a key, keycard, security code, mechanical actuation, or the like. The flange 70 may freely pivot toward and away from the supply drawers 14 and the front wall of the chassis 12 about the hinges 72 when the locking mechanism 74 is in the disengaged position. When the flange 70 is pivoted flush against front walls of the supply drawers 14 and the front wall 40 of the chassis 12, the locking mechanism 74 may be placed into the engaged position, such that the flange 70 is prevented from pivoting. Likewise, when the locking mechanism 74 is engaged and the flange 70 is prevented from pivoting, the supply drawers 14 and/or the cooling apparatus door 62 are all simultaneously prevented from opening.

The task light 20, as illustrated in FIG. 1, may be any light adjustably fixed to the chassis 12, and may be articulated to a particular height, angle, and orientation to assist medical personnel with the unique challenges of obstetric hemorrhaging. Specifically, the task light 20 may include a light bulb, electrical cords or connectors providing electricity from a power source to the lightbulb, and an adjustable, jointed, and/or bendable light stand fixed to the chassis 12. For example, the task light stand may include three or four articulating joints for positioning the task light 20 as needed during obstetric procedures. The task light stand may be fixed to the chassis 12 at or proximate to the back wall 38 thereof, and/or at or proximate to one of the side walls 42,44 thereof.

The display 22 may be fixed or adjustably attached to the chassis 12 or the IV pole 24 and may be configured for receiving signals from the portable ultrasound machine via a communication cable or other wireless communication devices. In general, the display 22 may comprise an electronic graphical interface operable to display visual graphics, images, video, text, etc. in response to external or internal processes and commands. For example, the display 22 may comprise conventional black and white, monochrome, or color display elements including CRT, TFT, LCD, and/or LED display devices. Further, the display 22 may comprise wired or wireless data transfer elements and/or communication ports such as a removable memory, data transceivers, or the like, to enable the user and other devices or parties to communicate with the display 22. In particular, the display 22 may include one or more ports configured for receiving and/or sending data from and to the portable ultrasound machine or other electronic devices configured to output displayable graphics, video, or other information.

In some embodiments of the invention, the display 22 may comprise and/or be communicably coupled with a user interface (not shown). The user interface may comprise one or more functionable inputs such as buttons, switches, scroll wheels, a touch screen associated with the display 22, voice recognition elements such as a microphone, pointing devices such as mice, touchpads, tracking balls, styluses, cameras such as a digital still or video camera, combinations thereof, or the like. For example, the display 22 may include or may be integrated with a touch screen display configured to enable a user to interact with the display by touching or pointing at display areas to provide information, make selections, and/or label something on the screen. In some embodiments of the invention, the user interface of the display 22 may comprise a pointer (e.g., stylus). Specifically, a position and orientation of the pointer may be tracked, as later described herein, so that when a user points at a particular area on the display, corresponding markings or labeling may be presented on the display 22.

The IV pole 24, as illustrated in FIG. 1, may be configured for hanging various medical items such as suction cups, breast pumps, IV fluid bags, and other medical items normally supported on a free-standing pole in hospital rooms. The IV pole 24 may include a primary pole 76 fixed to the chassis 12, a crossbar 78 fixed at or proximate to a top of the primary pole 76, and one or more hooks 80 onto which IV bags or the like may be attached. The IV pole 24 may be vertically adjustable via a height adjustment mechanism, such as a telescoping mechanism or other mechanical elongation or actuation mechanisms known in the art. For example, the primary pole 76 may include a top portion slidably actuatable relative to a bottom portion fixed to the chassis 12.

The power source 26, as illustrated in FIG. 9, may include an uninterruptable power source (UPS), one or more rechargeable batteries, or the like. The power source 26 may be electrically coupled with the task light 20, the cooling apparatus 16, and the scale 28, as well as other sensors, displays, and medical devices incorporated into the cart 10. For example, the power source 26 may also be electrically coupled with a portable ultrasound machine to provide power thereto. The power source 26 may be positioned within the chassis 12 and may be secured in a tray 82 mounted to the base 34 of the chassis 12, between the supply drawers 14 and the back wall 38 of the chassis 12. The power source 26 may include a plurality of outlets 84 configured for receiving standard electrical plugs, such that the cooling apparatus 16, scale 28, task light 20, display 22, and the like may be plugged directly therein. Furthermore, a power strip 86 or other collection of power outlets may be plugged into or electrically coupled to the power source 26 and then fixed and presented through an opening of the back wall 38 of the chassis 12, such that other electrical tools or accessories, beyond those integrated into the cart 10, may access the power source 26 as needed.

Figure 5:
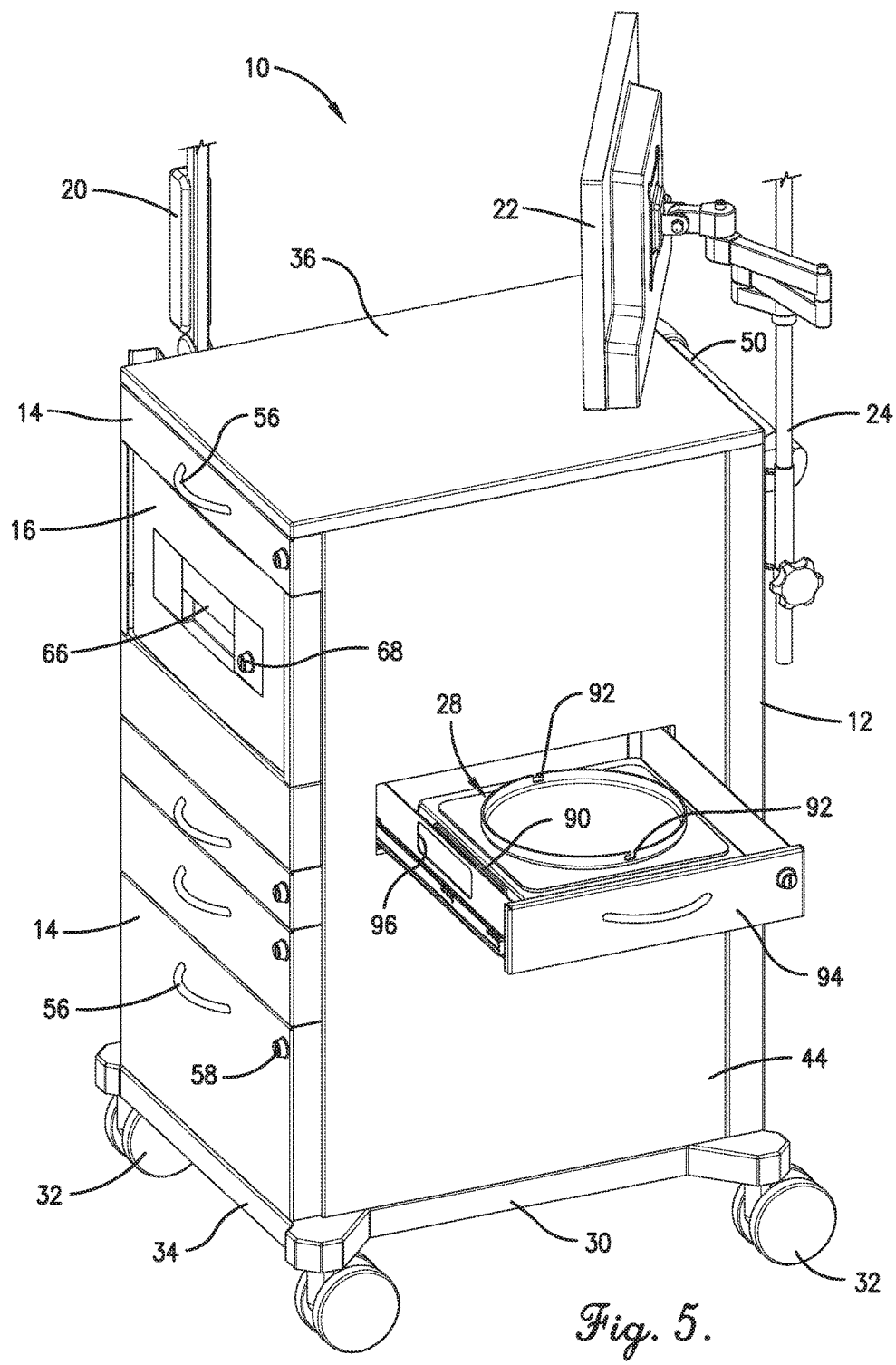
FIG. 5 is a side perspective view of the cart of FIG. 4 with the scale drawer open.

As illustrated in FIGS. 4 and 5, the scale 28 may be any scale known in the art with a scale-weighing surface 88 and a digital or mechanical display 90 configured to output the weight of any solid or liquid placed on the scale weighing surface 88. The scale 28 may generally have an overall low profile to allow the scale 28 to fit within one of the supply drawers 14. In some embodiments of the invention, the scale weighing surface 88 may be a flat square, rectangular, or circular platform. However, the scale 28 may have other shapes and configurations without departing from the scope of the invention. In some embodiments of the invention, the scale-weighing surface 88 may include a clamping device 92 for an open topped-enclosure, or alternatively may include a bowl, container, or protruding platform edges configured for preventing blood from dripping off sides of the scale-weighing surface.

The scale 28 may be mounted in one of the supply drawers 14, described above, referred to hereinafter as a scale drawer 94. The scale drawer 94 may extend outward through an opening in one of the side walls 44 of the chassis 12, such that others of the supply drawers 14 are not blocked while the scale 28 is being accessed and used to continuously weigh blood lost during hemorrhaging. For example, one of the supply drawers 14 may slide in and out of the chassis 12 along a first axis and the scale drawer 94 may slide in and out of the chassis 12 along a second axis that is substantially perpendicular to the first axis. The scale's low profile prevents the scale 28 from interfering with opening or closing of the scale drawer 94. The scale drawer 94 may include a translucent sidewall, a window 96, or an opening formed therethrough, providing a window viewable from the front of the chassis 12 when the scale drawer 94 is open. This allows a user to view the scale's display 90 during use, while the scale 28 remains in the open scale drawer 94. Alternatively, the scale 28 may be electrically coupled with a remote display (not shown) mounted or integrated into the front wall 40 of the chassis 12 or a front of one of the supply drawers 14 without departing from the scope of the invention, such that the scale drawer 94 does not require the window 96 or translucent sidewall in order to read the scale 28 reading. In other embodiments of the invention, the scale 28 may communicate directly or wirelessly with other electronic devices or displays, transmitting the weight sensed by the scale thereto, without departing from the scope of the invention.

Figure 6:
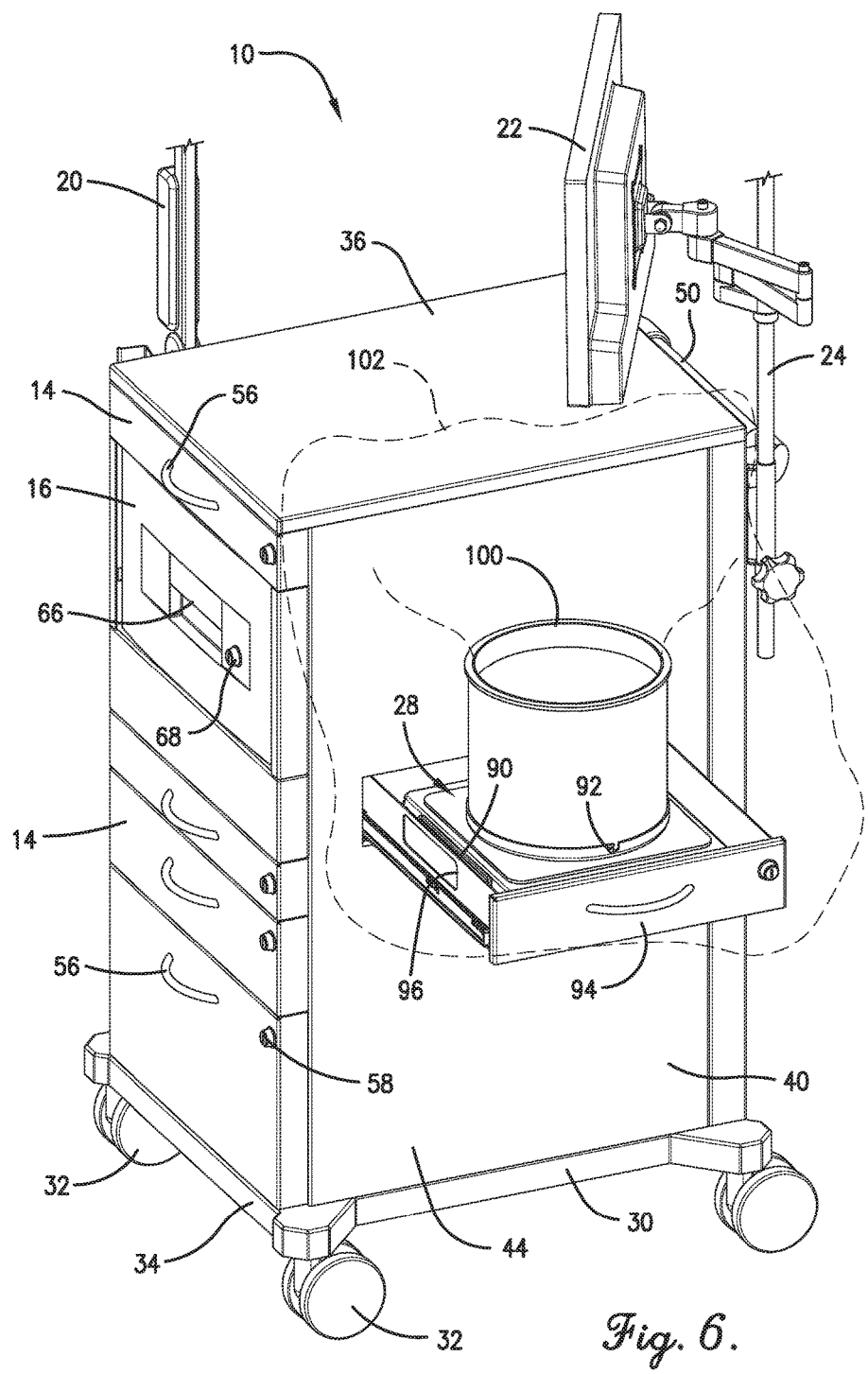
FIG. 6 is a side perspective view of the cart of FIG. 5 with a disposable container attached to a scale in the scale drawer.
Figure 10:
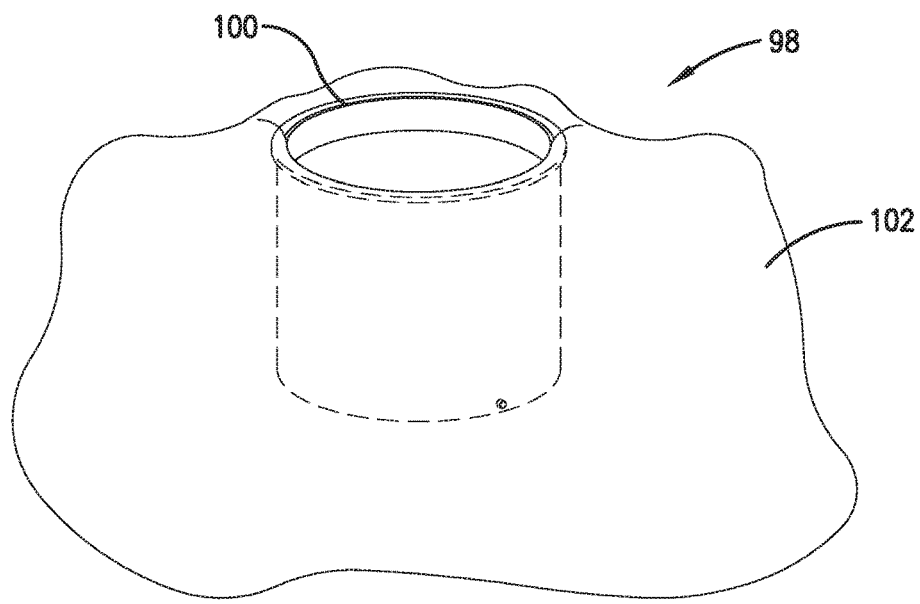
FIG. 10 is a front perspective view of a disposable container for attachment to the scale of FIG. 6, including a bag welded to and extending outward around an open-topped enclosure for receiving materials to be weighed by the scale.
Figure 11:
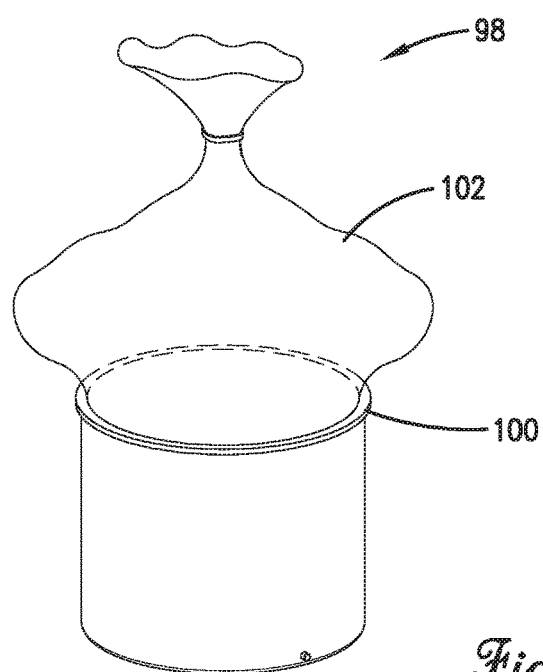
FIG. 11 is a front perspective view of the disposable container of FIG. 10 with the bag pulled upward and tied up for disposal.

In some embodiments of the invention, as illustrated in FIGS. 6, 10, and 11, the cart 10 may further include a disposable container 98 including an open-topped enclosure 100, such as a tray or bucket, and a disposable hazardous waste bag 102 integral with the open-topped enclosure 100. For example, a bottom end of the bag 102 may be welded along a top edge of the open-topped enclosure 100, with the remainder of the bag 102 contained inside the open-topped enclosure 100. The open-topped enclosure 100 may be attached to the scale weighing surface 88 after the scale drawer 94 is pulled out. This attachment may be accomplished using the clamping device 92, a locking mechanism, integrally-formed attachment components or protrusions, or any mechanical attachments known in the art, so that the open-topped enclosure 100 does not move during obstetric hemorrhage-related procedures. For example, the scale weighing surface 88 may include an upward-protruding clamping device sized and shaped to lock and secure the open-topped enclosure 100 to the scale weighing surface 88.

In use, the scale drawer 94 may be opened and the disposable container 98 may be placed onto the scale weighing surface 88. Then the clamping device 92 may secure the open-topped enclosure 100 thereof to the scale weighing surface 88, as illustrated in FIG. 6. Next, a top end of the bag 102 may be pulled out of the open-topped enclosure 100 and the bag 102 may be pulled around the scale drawer 94, and clipped or otherwise temporarily attached to the chassis 12 or other elements of the cart 10, thus shielding the cart 10 from the blood being placed into the open-topped enclosure 100 and weighed by the scale 28. For example, the bag 102 may substantially cover an entire exposed surface area of the scale drawer 94, above below, and to both sides of the scale drawer 94. Furthermore, the bag 102 may include a translucent portion (not shown) allowing the scale's display 90 to be read therethrough when the bag 102 is completely covering exposed surfaces of the scale drawer 94. During use, blood-soaked pads, sponges, rags, or other items may be placed in the open-topped enclosure 100 for weighing of the amount of blood lost by the patient. After use, the bag 102 may be detached from the cart 10, the bag 102 may be closed, and the open-topped enclosure 100 may be detached (e.g., unclamped) from the scale 28, as illustrated in FIGS. 10-11. Then the user may properly dispose of the entire disposable container 98.

By constructing an obstetric hemorrhage cart as described herein, medically-critical items may remain at a predetermined temperature to increase storage life. Furthermore, the locking bar described herein provides a fast, secure, and efficient way to secure and access medical supplies. The scale accessed from a side of the cart allows convenient tracking of the amount of blood a patient is losing in real time, both before, during, and after transfer to the operating room. This, along with the other features of the cart 10 described above, may advantageously reduce critical response time in obstetric bleeding situations by up to several minutes.

Although the invention has been described with reference to the embodiments illustrated in the attached drawing figures, it is noted that equivalents may be employed and substitutions made herein without departing from the scope of the invention as recited in the claims.

Having thus described various embodiments of the invention, what is claimed as new and desired to be protected by Letters Patent includes the following:

1. An obstetric hemorrhage cart for diagnosing, tracking, and treating obstetric hemorrhaging, the cart comprising:
   a chassis having a plurality of wheels attached thereto;
   a plurality of supply drawers supported on the chassis, wherein at least one of the supply drawers is slidable along a first axis toward the chassis to a closed orientation and slidable away from the chassis along the first axis to an open configuration;
   a cooling apparatus having a storage compartment with a door shiftable between an open position and a closed position and refrigeration components configured for cooling contents within the storage compartment;
   a locking bar pivotally attached to the chassis and shiftable between a blocking orientation that prevents opening of the supply drawers and the cooling apparatus door and a non-blocking position that allows the supply drawers and the cooling apparatus door to open;
   a scale drawer supported on the chassis and slidably openable along a second axis that is substantially perpendicular to the first axis;
   a scale supported in the scale drawer for accurately weighing blood lost by a patient during obstetric hemorrhaging, the scale having a weighing surface and a display;
   a positionable task light attached to the chassis having an adjustable light stand and a light source attached to the light stand; and
   a portable power supply electrically coupled the cooling apparatus, the scale, and the task light.

2. The obstetric hemorrhage cart of claim 1, wherein the scale drawer includes sidewalls and a window formed along or formed through at least one of the sidewalls, wherein the scale display is viewable through the window when the scale drawer is open.

3. The obstetric hemorrhage cart of claim 1, wherein the chassis includes a front wall, a back wall opposite the front wall, and two opposing side walls extending between the front wall and the back wall, wherein at least one of the supply drawers extends through the front wall, wherein the scale drawer extends through one of the side walls of the chassis.

4. The obstetric hemorrhage cart of claim 3, wherein the chassis further includes drawer mounts mechanically fixed to the side walls for slidably supporting the supply drawers, wherein the side walls each have a plurality of holes formed therein along a length of the side walls and configured for receiving mechanical fasteners for attaching the drawer mounts to the side walls, wherein the quantity and height of the supply drawers in the chassis is reconfigurable or customizable by moving the drawer mounts to different ones of the holes in the side walls.

5. The obstetric hemorrhage cart of claim 1, wherein the scale display is mounted on the front wall of the chassis.

6. The obstetric hemorrhage cart of claim 1, further comprising an electronic display electrically coupled to the portable power supply and configured to communicably couple with a portable ultrasound machine.

7. The obstetric hemorrhage cart of claim 1, wherein the portable power supply is a rechargeable uninterruptible power supply mounted within the chassis and behind at least one of the supply drawers.

8. The obstetric hemorrhage cart of claim 1, further comprising a power strip of outlets mounted on the chassis and electrically coupled with the portable power supply.

9. The obstetric hemorrhage cart of claim 1, wherein the chassis includes a top surface formed at least partially of antimicrobial material.

10. The obstetric hemorrhage cart of claim 1, further including a handle attached to the chassis and formed at least partially of an antimicrobial material.

11. The obstetric hemorrhage cart of claim 1, wherein the chassis includes a front wall through which the supply drawers extend, wherein the cooling apparatus door opens through the front wall.

12. The obstetric hemorrhage cart of claim 11, further comprising a disposable hazardous waste bag attached to the open-topped enclosure and sized and configured to substantially surround a majority of the scale drawer when the scale drawer is open.

13. The obstetric hemorrhage cart of claim 1, further comprising an open-topped enclosure removably attached to the weighing surface of the scale for receiving materials to be weighed by the scale.

14. The obstetric hemorrhage cart of claim 1, further comprising an IV pole fixed to the chassis and having a height adjustment mechanism.

15. The obstetric hemorrhage cart of claim 1, further comprising a drawer lock coupled with each supply drawer, wherein each drawer lock is shiftable between a locked position that prevents its supply drawer from opening and an unlocked position that allows its supply drawer to open.

16. An obstetric hemorrhage cart for diagnosing, tracking, and treating obstetric hemorrhaging, the cart comprising:
- a chassis having a base, a top opposing the base, a first side wall extending between the top and the base, a second side wall opposing the first side wall, a front wall extending between the first and second side walls, and a back wall opposing the front wall;
- a plurality of wheels attached to the chassis at the base;
- a plurality of drawer mounts mechanically attached to the first side wall and the second side wall;
- a plurality of supply drawers, each supply drawer slidably attached to at least one of the drawer mounts;
- at least one drawer lock shiftable between a locked position preventing at least one of the supply drawers from opening and an unlocked position allowing at least one of the supply drawers to open;
- a cooling apparatus comprising:
  - a storage compartment with a cooling apparatus door,
  - a cooling apparatus door lock shiftable between a locked position preventing the cooling apparatus door from opening and an unlocked position allowing the cooling apparatus door to open, and
  - refrigerating components that cool a temperature of the storage compartment to a predetermined temperature;
- a locking bar pivotally attached to the chassis and shiftable between a blocking orientation preventing opening of the supply drawers and the cooling apparatus door and a non-blocking orientation allowing the supply drawers and the cooling apparatus door to open, wherein the locking bar is selectively lockable in the blocking orientation;
- a scale drawer slidable into the chassis at the first side wall or the second side wall of the chassis in a closed position and slidable out of the first side wall or the second side wall of the chassis in an open position;
- a medical scale mounted in the scale drawer and including a weighing surface and a scale display, wherein the scale drawer includes a transparent sidewall or window through which the scale display is viewable by a person facing the front of the chassis when the scale drawer is in the open position;
- an open-topped enclosure removably attached to the weighing surface of the scale for receiving materials to be weighed by the scale;
- a positionable task light attached to the chassis and having a jointed, adjustable light stand and at least one light bulb attached to the light stand; and
- a portable power supply electrically coupled to the cooling apparatus, the scale, and the task light, wherein the portable power supply is a rechargeable uninterruptible power supply.

17. The obstetric hemorrhage cart of claim 16, further comprising a disposable hazardous waste bag attached to the open-topped enclosure and sized and configured to substantially surround a majority of the scale drawer when the scale drawer is open.

18. The obstetric hemorrhage cart of claim 16, further comprising a power strip of outlets mounted to the back wall of the chassis and electrically coupled to the portable power supply, wherein the portable power supply is mounted within the chassis and behind at least one of the supply drawers.

19. The obstetric hemorrhage cart of claim 16, further comprising an IV pole fixed to the chassis and having a height adjustment mechanism and an electronic display physically coupled to the IV pole or the chassis and electrically coupled to the portable power supply, wherein the electronic display is configured to communicably couple with a portable ultrasound machine.

20. An obstetric hemorrhage cart for diagnosing, tracking, and treating obstetric hemorrhaging, the cart comprising:
- a chassis having a base, a top surface opposing the base and composed of an antimicrobial material, a first side wall extending between the top surface and the base, a second side wall opposing the first side wall, a front wall extending between the first and second side walls, and a back wall opposing the front wall;
- a plurality of wheels attached to the chassis at the base;
- a handle attached to the chassis and configured for pushing or pulling the chassis, thus causing rotation of the wheels engaged with a floor for transport of the chassis;
- a plurality of drawer mounts mechanically attached to the first side wall and the second side wall and reconfigurable along a height of the first side wall and the second side wall;
- a plurality of supply drawers, each supply drawer slidably attached to at least one of the drawer mounts, wherein each of the supply drawers include a drawer lock shiftable between a locked position preventing one of the supply drawers from opening and an unlocked position allowing one of the supply drawers to open;
- a cooling apparatus comprising:
  - a storage compartment with a cooling apparatus door shiftable between an open position and a closed position,
  - a cooling apparatus door lock shiftable between a locked position preventing the cooling apparatus door from opening and an unlocked position allowing the cooling apparatus door to open, and
  - refrigerating components that cool a temperature of the storage compartment to a predetermined temperature;
- a locking bar pivotally attached to the chassis and shiftable between a blocking orientation simultaneously preventing opening of the supply drawers and the cooling apparatus door and a non-blocking orientation allowing the supply drawers and the cooling apparatus door to open, wherein the locking bar is selectively lockable in the blocking orientation;
- a scale drawer slidable into the chassis at the first side wall or the second side wall of the chassis to a closed position and slidable out of the first side wall or the second side wall of the chassis to an open position;
- a medical scale mounted in the scale drawer and including a weighing surface and a scale display, wherein the scale drawer includes a transparent sidewall or window through which the scale display is viewable by a person facing the front of the chassis when the scale drawer is in the open position;
- an open-topped enclosure removably attached to the weighing surface of the scale for receiving materials to be weighed by the scale;
- a disposable hazardous waste bag attached to the open-topped enclosure and sized and configured to substantially surround a majority of the scale drawer when the scale drawer is open;

a positionable task light attached to the chassis and having a jointed, adjustable light stand and at least one light bulb attached to the light stand;

a portable power supply mounted within the chassis and behind at least one of the supply drawers, wherein the portable power supply is electrically coupled to at least one of the cooling apparatus, the scale, and the task light, wherein the portable power supply is a rechargeable uninterruptible power supply;

a power strip of outlets mounted to the back wall of the chassis and electrically coupled to the portable power supply;

an IV pole fixed to the chassis and having a height adjustment mechanism; and an electronic display physically coupled to the IV pole or the chassis and electrically coupled to the portable power supply, wherein the electronic display is configured to communicably couple with a portable ultrasound machine.

* * * * *

UNITED STATES PATENT AND TRADEMARK OFFICE
CERTIFICATE OF CORRECTION

PATENT NO. : 10,045,829 B1
APPLICATION NO. : 15/728639
DATED : August 14, 2018
INVENTOR(S) : Scott Norman et al.

Page 1 of 1

It is certified that error appears in the above-identified patent and that said Letters Patent is hereby corrected as shown below:

On the Title Page

Item (73), the Assignee reads:
"Neonatal Products Group, Inc."
Should read:
"Neonatal Product Group, Inc."

Signed and Sealed this
Fourth Day of June, 2019

Andrei Iancu
*Director of the United States Patent and Trademark Office*